United States Patent
Vu et al.

(10) Patent No.: US 12,310,576 B2
(45) Date of Patent: May 27, 2025

(54) QUICKDRAW KNOT PUSHER: SIDE LOADING KNOT PUSHER

(71) Applicant: Conmed Corporation, Largo, FL (US)

(72) Inventors: Thien Vu, Pinellas Park, FL (US); Ryo Isshiki, Largo, FL (US)

(73) Assignee: Conmed Corporation, Utica, NY (US)

( * ) Notice: Subject to any disclaimer, the term of this patent is extended or adjusted under 35 U.S.C. 154(b) by 441 days.

(21) Appl. No.: 17/638,338

(22) PCT Filed: Sep. 3, 2020

(86) PCT No.: PCT/US2020/049124
§ 371 (c)(1),
(2) Date: Feb. 25, 2022

(87) PCT Pub. No.: WO2021/046170
PCT Pub. Date: Mar. 11, 2021

(65) Prior Publication Data
US 2022/0287706 A1    Sep. 15, 2022

Related U.S. Application Data

(60) Provisional application No. 62/895,160, filed on Sep. 3, 2019.

(51) Int. Cl.
*A61B 17/04* (2006.01)
*A61B 17/00* (2006.01)

(52) U.S. Cl.
CPC ............... *A61B 17/0469* (2013.01); *A61B 2017/00367* (2013.01); *A61B 2017/00424* (2013.01); *A61B 2017/0474* (2013.01)

(58) Field of Classification Search
CPC ........... A61B 2017/00349; A61B 2017/00353; A61B 2017/00358; A61B 17/0469;
(Continued)

(56) References Cited

U.S. PATENT DOCUMENTS 6,045,561 A * 4/2000 Marshall ............ A61B 17/0469
606/139
9,247,935 B2    2/2016 George et al.
(Continued)

FOREIGN PATENT DOCUMENTS

JP    2000-512193 A2    9/2000
JP    2018-015514 A2    2/2018
WO    2018049138    3/2018

OTHER PUBLICATIONS

International Search Report Form PCT/ISA/220, International Application No. PCT/US2020/049124 pp. 1-19, Dated Nov. 9, 2020.
(Continued)

*Primary Examiner* — Shaun L David
*Assistant Examiner* — Rachael L Geiger
(74) *Attorney, Agent, or Firm* — Bond, Schoeneck & King, PLLC; Frederick J. M. Price

(57) ABSTRACT

A knot pusher for quickly loading suture without needing to thread a distal end. The knot pusher includes an actuator housing having an actuator moveable between an open position and a closed position and an elongated tube extending from the actuator housing. The knot pusher includes at least two slots, a gate slot extending through the elongated tube and a suture loading slot extending through the elongated tube and traversing the gate slot. A moveable gate cross bar is connected to the actuator such that the gate cross bar moves with the actuator between the open position and the closed position. When the actuator is in the closed position, the gate cross bar extends through at least a portion of the suture loading slot. The knot pusher may also include an ergonomic loop handle that enforces the correct orientation of the knot pusher for use.

20 Claims, 14 Drawing Sheets

(58) Field of Classification Search
CPC .......... A61B 2017/00367; A61B 2017/00424; A61B 2017/0474; A61B 17/0483; A61B 2017/2911; A61B 2017/0475; A61B 2017/0472; A61B 2017/0477
See application file for complete search history.

(56) References Cited

U.S. PATENT DOCUMENTS

| | | |
|---|---|---|
| 10,299,786 B2 | 5/2019 | Levine et al. |
| 2015/0088163 A1* | 3/2015 | George .............. A61B 17/0467 606/138 |
| 2016/0038141 A1 | 2/2016 | Levine et al. |
| 2016/0374749 A1 | 12/2016 | Terzariol |
| 2018/0235600 A1* | 8/2018 | Nachmias .......... A61B 17/0467 |

OTHER PUBLICATIONS

Japanese Office Action, Application No. 2022-513903, Dated Feb. 3, 2023, pp. 1-7.
Translated Chinese Notice of Division, App. No. 202080061921.2, dated Jan. 31, 2024, pp. 1-2.

* cited by examiner

QUICKDRAW KNOT PUSHER: SIDE LOADING KNOT PUSHER

CROSS-REFERENCES TO RELATED APPLICATIONS

This application is a national stage application under 35 U.S.C. 371 based on international patent application PCT/US20/49124 filed on Sep. 3, 2020, which claims priority to U.S. Provisional Patent Application Ser. No. 62/895,160, filed on Sep. 3, 2019 and entitled "Quickdraw Knot Pusher: Side Loading Knot Pusher," the entireties of which are incorporated herein by reference.

BACKGROUND OF THE INVENTION

1. Field of the Invention

The present invention relates to arthroscopic knot tying and, more particularly, to a knot pusher device for quickly and securely loading suture to facilitate arthroscopic knot tying.

2. Description of Related Art

Many common surgical procedures involve the repair and reconstruction of torn or damaged soft tissue. For example, in common arthroscopic surgical procedures, a replacement graft ligament is secured at the site of the original, now damaged, ligament. Suspensory graft fixation devices have been developed to secure the graft ligament in a bone tunnel. Suspensory graft fixation devices work by lying transversely across the opening of a bone tunnel and generally take the form of an elongated anchor member which suspends a graft retaining loop from a fixation point on the surface of a bone to which the graft is to be attached. The graft retaining loop is composed of suture and is secured with a knot formed in the suture.

In other arthroscopic procedures, expanding rigid anchors or soft, all-suture anchors are used to attach soft tissue to bone. Often, the anchors are attached to suture and deployed by tensioning the suture. To secure the deployed anchor, a knot is created in the suture. Knots in suture for securing a graft or anchor in arthroscopic procedures is accomplished by hand or via a driver/inserter device. Driver/inserter mechanisms are preferable to hand-set deployment of arthroscopic anchors and tying of graft retaining suture loops because they often require less visibility and loading steps by the user. However, current driver/inserter devices require that the suture be threaded on its distal end by the user prior to use, which takes time and small, careful movements.

Therefore, there is a need for a device for pushing a knot into a surgical site wherein suture is easily loaded onto the device.

The term "suture" as used herein may be any type of filamentous material such as a biocompatible or bioabsorbable filament, ribbon, tape, woven or non-woven material.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention are directed to a knot pusher. An embodiment of the knot pusher includes an actuator housing having an actuator moveable between an open position and a closed position and an elongated tube extending from the actuator housing. The knot pusher includes at least two slots, a gate slot extending through the elongated tube and a suture loading slot extending through the elongated tube and traversing the gate slot. A moveable gate cross bar is connected to the actuator such that the gate cross bar moves with the actuator between the open position and the closed position. When the actuator is in the closed position, the gate cross bar extends through at least a portion of the suture loading slot.

According to another aspect, the knot pusher includes an actuator housing having an actuator moveable between an open position and a closed position and an elongated tube extending from the actuator housing. The knot pusher includes three slots, a gate slot extending through the elongated tube, a suture exit slot extending through the elongated tube, and a suture loading slot extending through the elongated tube and traversing the gate slot. A moveable gate cross bar is connected to the actuator such that the gate cross bar moves with the actuator between the open position and the closed position. When the actuator is in the closed position, the gate cross bar extends through at least a portion of the suture loading slot.

According to yet another aspect, the knot pusher includes a handle having an actuator housing extending from a ring-shaped end. There is an actuator at least partially within the actuator housing and moveable between an open position and a closed position. An elongated tube extends from the actuator housing. The knot pusher includes at least two slots, a gate slot extending through the elongated tube and a suture loading slot extending through the elongated tube and traversing the gate slot. A moveable gate cross bar is connected to the actuator such that the gate cross bar moves with the actuator between the open position and the closed position. When the actuator is in the closed position, the gate cross bar extends through at least a portion of the suture loading slot.

These and other aspects of the invention will be apparent from and elucidated with reference to the embodiment(s) described hereinafter.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
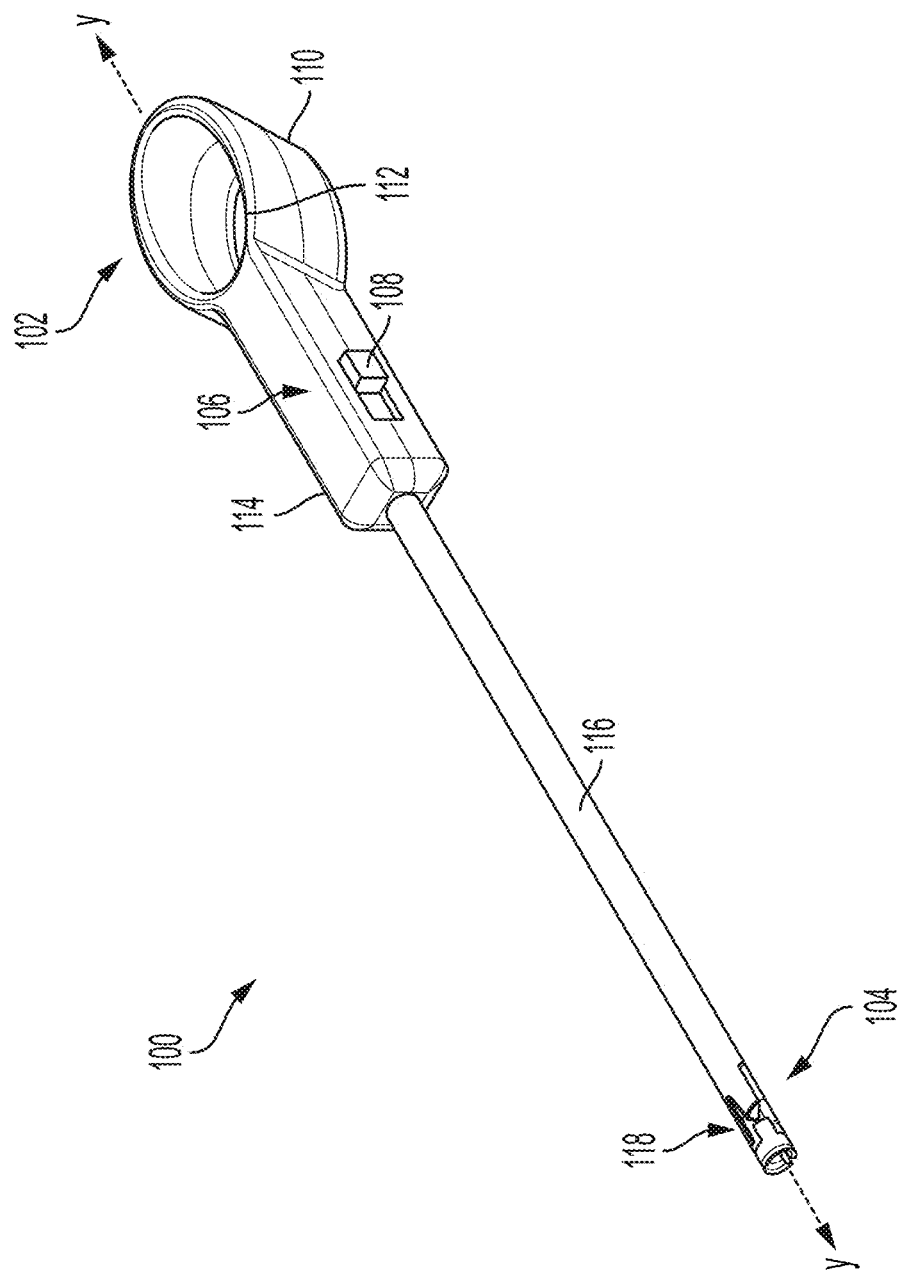
FIG. 1 is an isometric view schematic representation of a knot pusher, according to an embodiment.

Referring now to the figures, wherein like reference numerals refer to like parts throughout, FIG. 1 shows an isometric view schematic representation of a knot pusher 100, according to an embodiment. The knot pusher 100 has a proximal end 102 and distal end 104. At the proximal end 102, the knot pusher 100 has a handle 106. The handle 106 has a ring-shaped end 110 with an aperture 112 extending therethrough (also referred to as a "loop end"). The handle 106 also has a rectangular actuator housing 114 extending distally from the ring-shaped end 110. The actuator housing 114 has a moveable actuator 108 that is configured to move proximally toward and distally away from the ring-shaped end 110. The ring-shaped end 110 is provided for ergonomic and orientation benefits, as will be described in detail below. As also shown in FIG. 1, an elongated tube 116 extends along a central longitudinal y-y axis from the handle 106 (i.e., from the actuator housing 114) to the distal end 104. At the distal end 104 of the knot pusher 100, the elongated tube 116 comprises a loading zone 118 for attaching suture (not shown) to the knot pusher 100.

Figure 2:
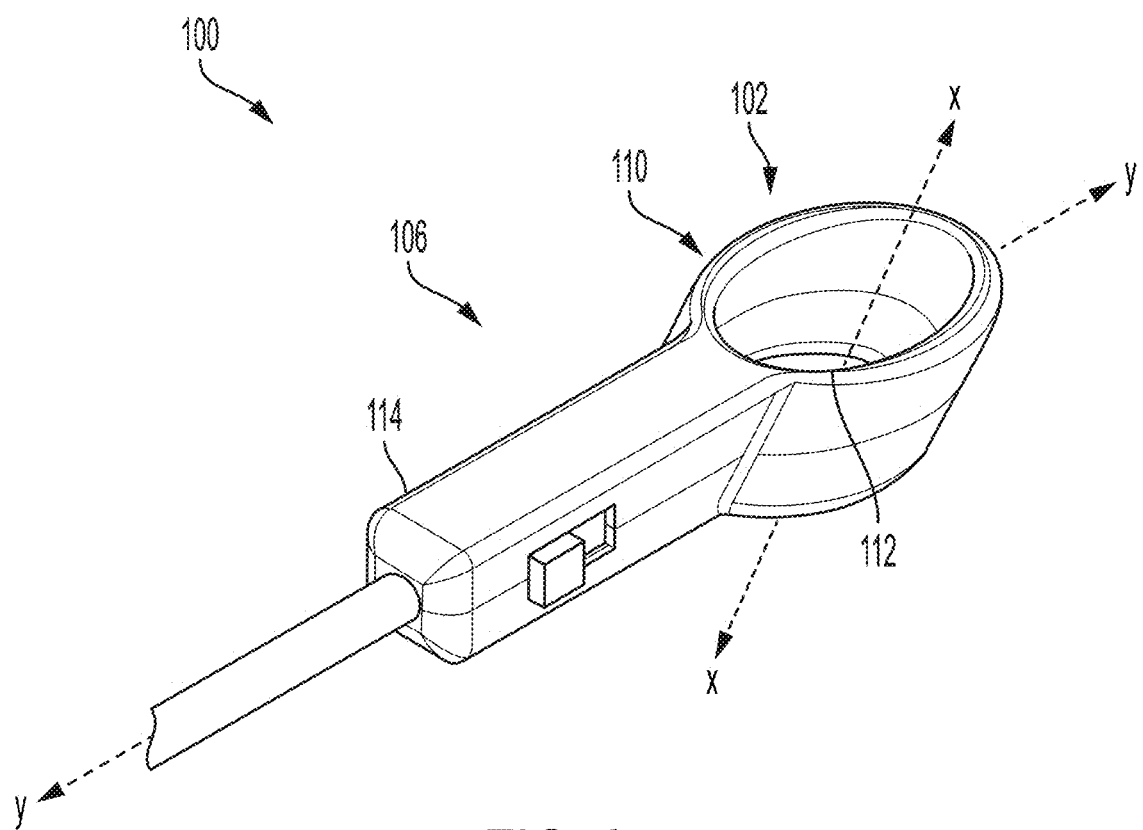
FIG. 2 is close-up, isometric view schematic representation of a handle of the knot pusher, according to an embodiment.

Referring now to FIG. 2, there is shown a close-up, isometric view schematic representation of the handle 106 of the knot pusher 100, according to an embodiment. As stated above, the handle 106 has the ergonomic, ring-shaped end 110 at the proximal end 102 of the knot pusher 100. The geometry of the ring-shaped end 110 allows for a user's thumb to rest naturally in the aperture 112 while in use. As shown in FIG. 2, and more clearly in FIG. 3, the ring-shaped end 110 is angled relative to the actuator housing 114.

Figure 3:
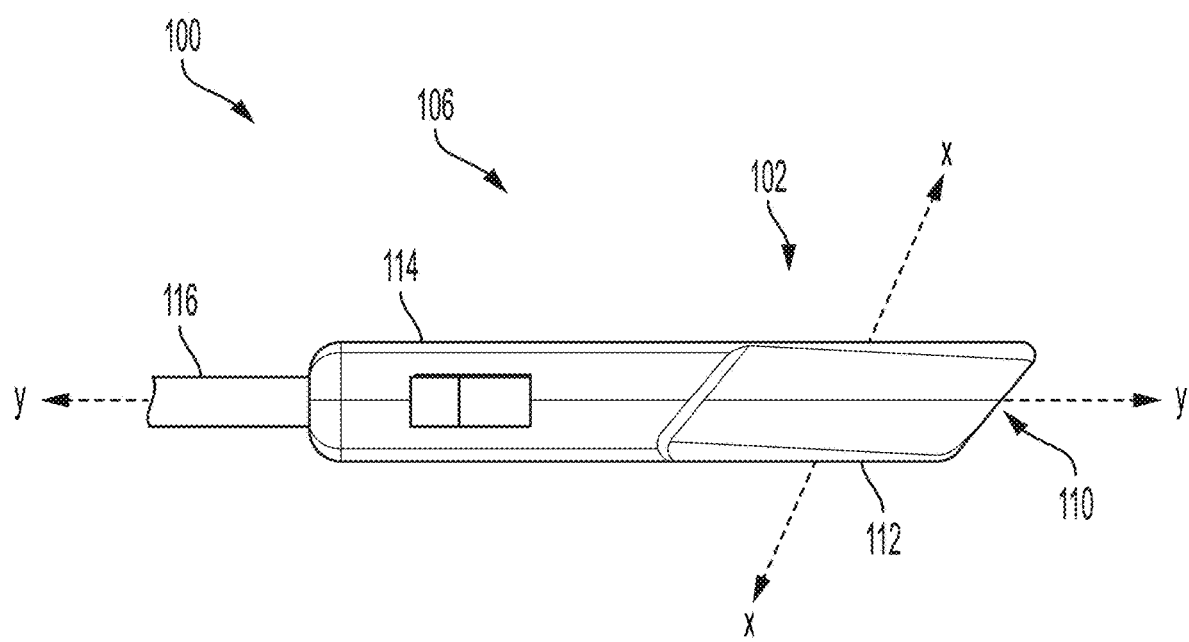
FIG. 3 is a close-up, side view schematic representation of a handle of the knot pusher, according to an embodiment.

The aperture 112 extending through the ring-shaped end 110 has a central x-x axis extending therethrough. The central x-x axis is at angle relative to the central longitudinal y-y axis extending through the elongated tube 116. In FIG. 3, the central x-x axis is at angle between 0 and 90 degrees relative to the central longitudinal y-y axis. The angle of the ring-shaped end 110 provides a one-way functionality that forces the user to orient the knot pusher 100 in the correct position in order to fit his or her thumb in the aperture 112, regardless of the hand used (left or right). Thus, the angle of the ring-shaped end 110 not only provides an ergonomic grip but also forces proper orientation of the knot pusher 100 when manipulated by the user.

Figure 4:
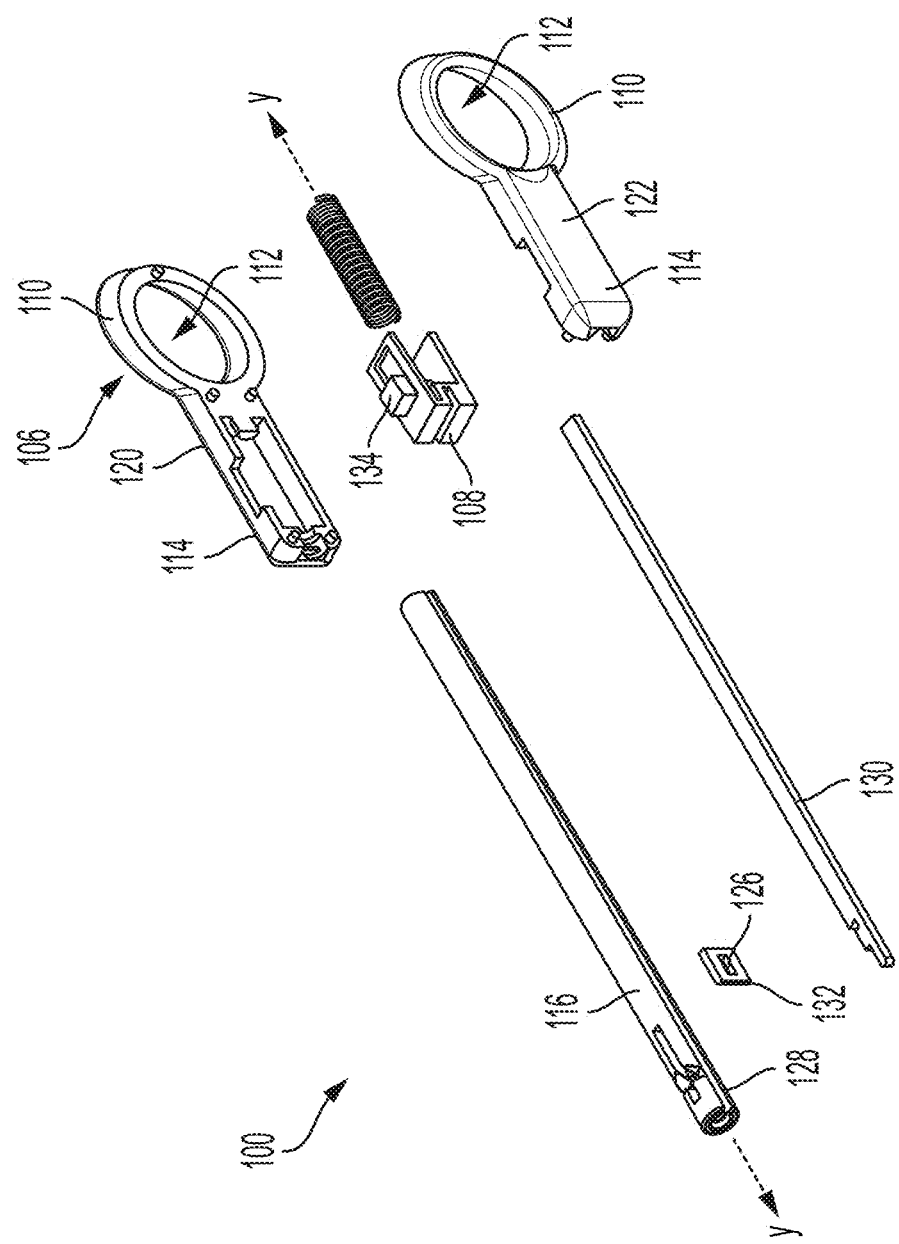
FIG. 4 is an exploded view schematic representation of the knot pusher, according to an embodiment.

Turning now to FIG. 4, there is shown an exploded view schematic representation of the knot pusher 100, according to an embodiment. In the depicted embodiment, the handle 106 is comprised of two pieces, a first body portion 120 and a second body portion 122. The first and second body portions 120, 122 each comprise the ring-shaped end 110 with the aperture 112 extending therethrough. Additionally, the first and second body portion 120, 122 each comprise a half of the rectangular actuator housing 114. The actuator housing 114 houses the moveable actuator 108. In the depicted embodiment, the moveable actuator 108 is spring-loaded, i.e., biased by a spring 124 within the actuator housing 114. The moveable actuator 108 comprises an actuator button 134 extending out from the actuator housing 114, as shown in FIG. 1.

Referring back to FIG. 4, the elongated tube 116 is cannulated such that it has an inner volume. An elongated channel 128 extends through an exterior of the elongated tube 116 and into the inner volume. The elongated channel 128 extends along or parallel to the central longitudinal y-y axis. The elongated tube 116 additionally comprises a detachable and/or moveable gate bar 130. The gate bar 130 is a narrow, flat rod that is sized and configured to fit within the elongated channel 128. The elongated tube 116 also includes a gate cross bar 132. In the depicted embodiment, the gate cross bar 132 is rectangular with an aperture 126 extending therethrough. The gate bar 130 and the gate cross bar 132 are attached to and move with the actuator 108 to move the loading zone 118 between an open position and a closed position.

Figure 5:
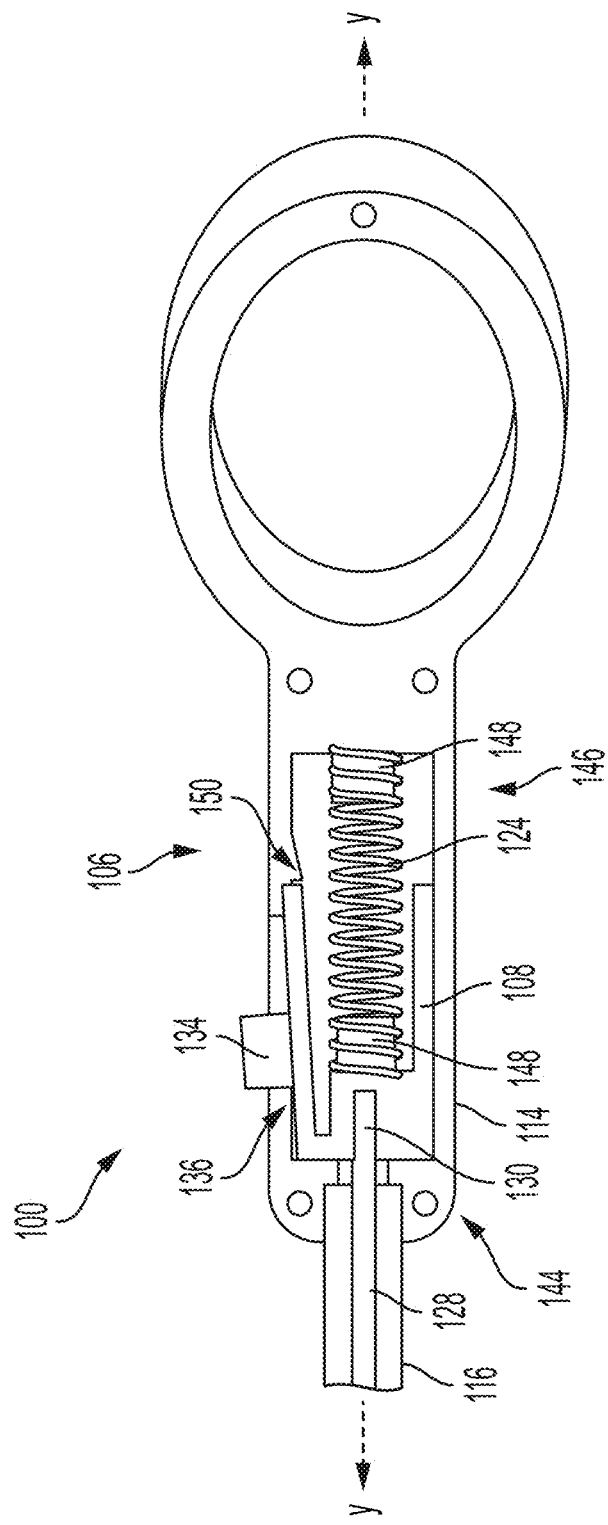
FIG. 5 is a close-up and partial cross-sectional view schematic representation of the handle of the knot pusher, according to an embodiment.

Turning now to FIG. 5, there is shown a close-up and partial cross-sectional view schematic representation of the handle 106 of the knot pusher 100, according to an embodiment. As shown, the elongated tube 116 is fixed to the handle 106 at a distal end 144 of the actuator housing 114. In the depicted embodiment, the elongated tube 116 if fixed within the actuator housing 114; however, it is contemplated that it can be attached flush with the exterior of the distal end 144. The gate bar 130 is shown within the elongated channel 128 of the elongated tube 116. The gate bar 130 is connected to the actuator 108, as shown in FIG. 5. Thus, the gate bar 130 moves with the actuator 108.

Still referring to FIG. 5, the actuator 108 is connected to the spring 124 and the spring 124 is connected to a proximal end 146 of the actuator housing 114. The spring 124 is connected to a pair of spring guides 148, one on the proximal end 146 of the actuator housing 114 and one on the actuator 108, which keeps the force vector of the spring 124 axial. The spring 124 in FIG. 5 is biased toward the distal end 144 of the actuator housing 114. Thus, the gate bar 130 is biased in the distal direction, i.e., the closed position of the loading zone 118.

As stated above, the purpose of the spring-biased actuator 108 is to move the loading zone 118 between the open and closed positions. The actuator 108, as shown in FIG. 5, and has an outer surface 136 connected to the actuator button 134 that extends at an angle relative to the central longitudinal y-y axis. The angled outer surface 136 of the actuator 108 allows the actuator 108 to hold the spring 124 in its compressed form when the actuator button 134 is moved proximally to the open position. The user must maintain force on the actuator button 134 in the proximal direction to maintain the open position of the loading zone 118. When the actuator button 134 is released, it automatically returns the loading zone 118 to the closed position. When the actuator button 134 is released, the spring 124 relaxes to an uncompressed form, moving the actuator button 134 in the distal direction until the outer surface 136 of the actuator 108 interfaces with a catch 150 (e.g., protrusion or other obstructive feature) on the actuator housing 114. This prevents the actuator 108 from moving without engagement of the actuator button 134 and also prevents the actuator 108 from moving when force is applied to the gate bar 130 during use.

Figure 6:
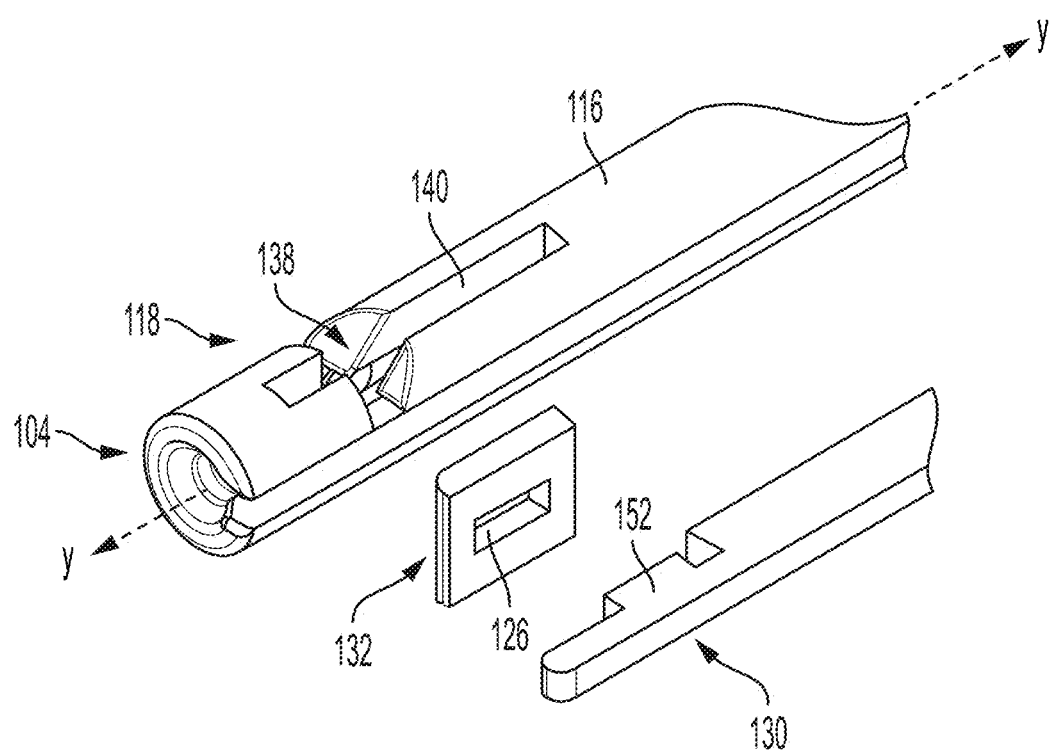
FIG. 6 is a close-up, exploded view schematic representation of the loading zone, according to an embodiment.

Referring now to FIG. 6, there is shown a close-up, exploded view schematic representation of the loading zone 118, according to an embodiment. The elongated tube 116 includes the gate cross bar 132 connected to the gate bar 130. The gate bar 130 includes a feature 152 (e.g., protrusion) that extends through the aperture 126 in the gate cross bar 132. Connection of the gate bar 130 and the gate cross bar 132 via extension of the feature 152 through the aperture 126 facilitates movement of the gate cross bar 132 together with the gate bar 130. Thus, as the actuator 108 moves the gate bar 131) connected thereto (FIG. 5), the gate cross bar 132 moves. The gate cross bar 132 also serves to restrict the motion of the gate bar 130 to be only along the elongated tube 116. The gate bar 130 and the gate cross bar 132 are assembled inside the knot pusher 100 (as shown in the Figures) and bonded.

Figure 10:
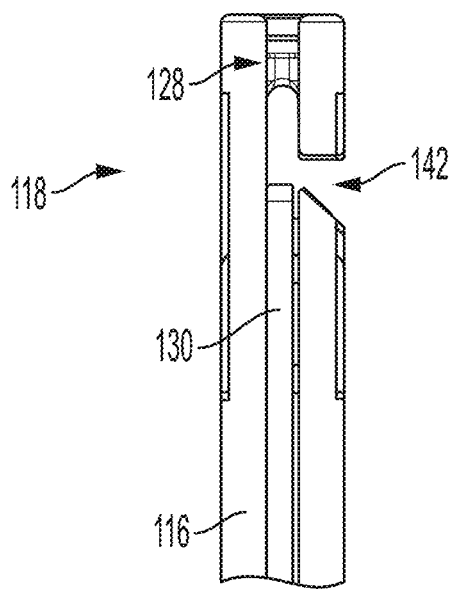
FIG. 10 is a close-up, bottom view schematic representation of the loading zone of the knot pusher, according to an embodiment.

Still referring to FIG. 6, the loading zone 118 of the elongated tube 116 also comprises a gate slot 140. The gate slot 140 extends through the elongated tube 116 to the inner volume (FIG. 10). As shown in FIG. 6, the gate slot 140 is slightly spaced from the distal end 104 of the elongated tube 116. The gate slot 140 extends along or parallel to the central longitudinal y-y axis. The gate slot 140 is rectangular in the embodiment shown in FIG. 6 and is sized and configured to facilitate movement of the gate cross bar 132 therein. As the gate bar 130 moves with engagement of the actuator 108, the gate cross bar 132 moves proximally or distally within the gate slot 140. Thus, the gate slot 140 restricts proximal and distal movement of the gate cross bar 132 and, consequently, the gate bar 130.

Figure 7:
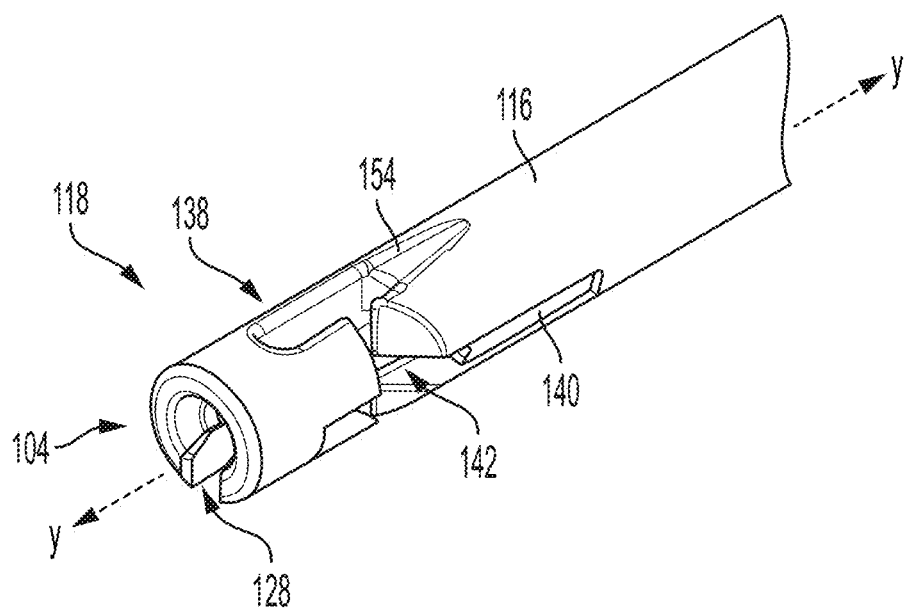
FIG. 7 is a close-up, isometric view schematic representation of a loading zone of the knot pusher, according to an embodiment.
Figure 8:
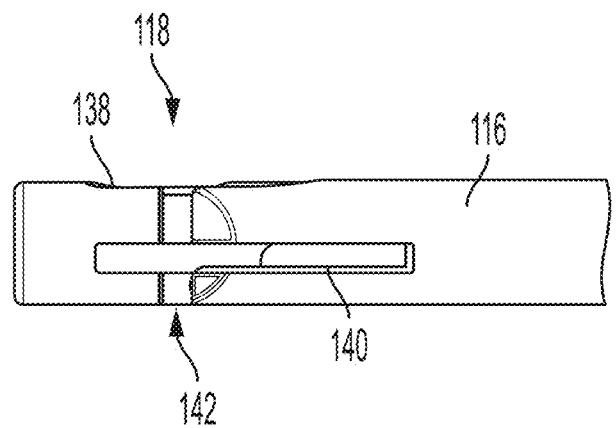
FIG. 8 is a close-up, side view schematic representation of the loading zone of the knot pusher, according to an embodiment.
Figure 9:
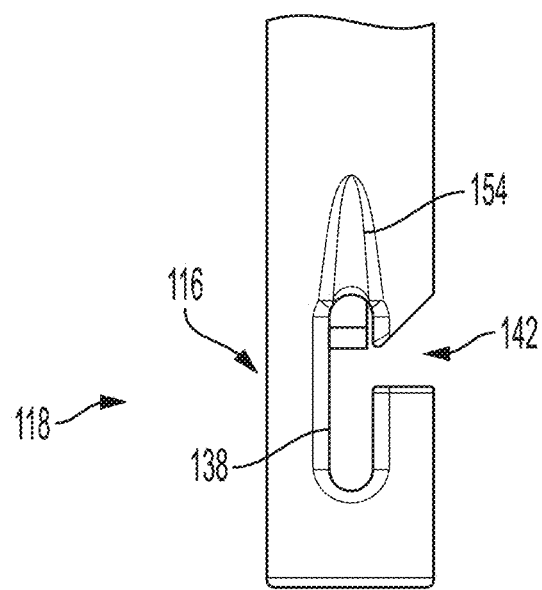
FIG. 9 is a close-up, top view schematic representation of the loading zone of the knot pusher, according to an embodiment.

Turning now to FIGS. 7-10, there are shown various close-up views schematic representations of the loading zone 118 of the knot pusher 100, according to an embodiment. At the loading zone 118 on the elongated tube 116, there is a suture exit slot 138, as shown in FIGS. 6-7 and 9. The suture exit slot 138 extends through the elongated tube 116 and extends to a tapered or pointed recess 154 in the elongated tube 116. The suture exit slot 138 is substantially rectangular and extends along or parallel to the central longitudinal y-y axis.

As shown in FIG. 7, the suture exit slot 138 is approximately 180 degrees (radially) along the elongated tube 116 from the elongated channel 128. In other words, the suture exit slot 138 is substantially parallel to the elongated channel 128. As also shown in FIG. 7, the suture exit slot 138 is slightly spaced from the distal end 104 of the elongated tube 116, whereas the elongated channel 128 extends through the distal end 104 of the elongated tube 116. The gate slot 140 is approximately 90 degrees (radially) along the elongated tube 116 from the suture exit slot 138, as depicted in FIG. 7.

In FIGS. 7-10, the loading zone 118 includes a suture loading slot 142 extending between the gate slot 140 and the suture exit slot 138. The suture loading slot 142 is a gap, cut, aperture, or other opening in the elongated tube 116. The suture loading slot 142 is substantially perpendicular to the gate slot 140, suture exit slot 138, and central longitudinal y-y axis, as shown in FIG. 8.

Figure 11A:
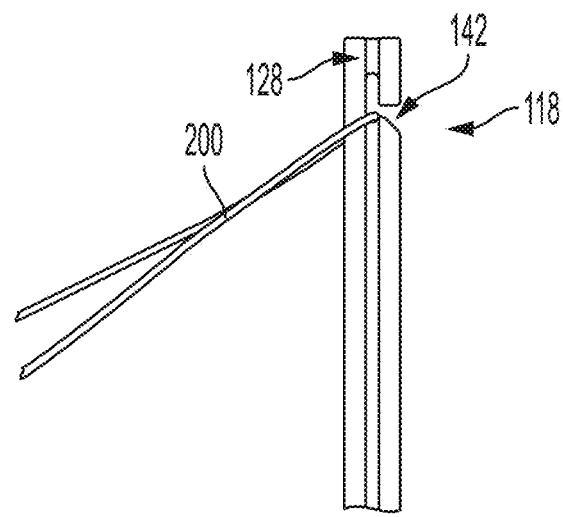
FIG. 11A is a bottom view of the loading zone in an open position with suture extending therethrough, according to an embodiment.
Figure 11B:
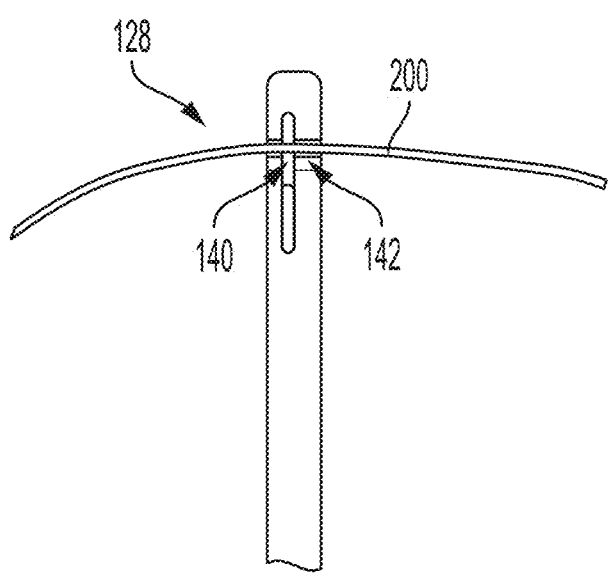
FIG. 11B is a side view of the loading zone in the open position with suture extending therethrough, according to an embodiment.

Referring now to FIGS. 11A and 11B, there is shown a bottom view and a side view, respectively, of the loading zone 118 in the open position with suture 200 extending therethrough, according to an embodiment. Suture 200 is loaded into the suture loading slot 142 over the gate slot 140, as shown in FIG. 11B. When loaded, the suture 200 extends through the elongated channel 128, as shown in FIG. 11A. When the suture 200 is loaded, the loading zone 118 is in the open position (via the actuator 108, as described above).

Figure 12:
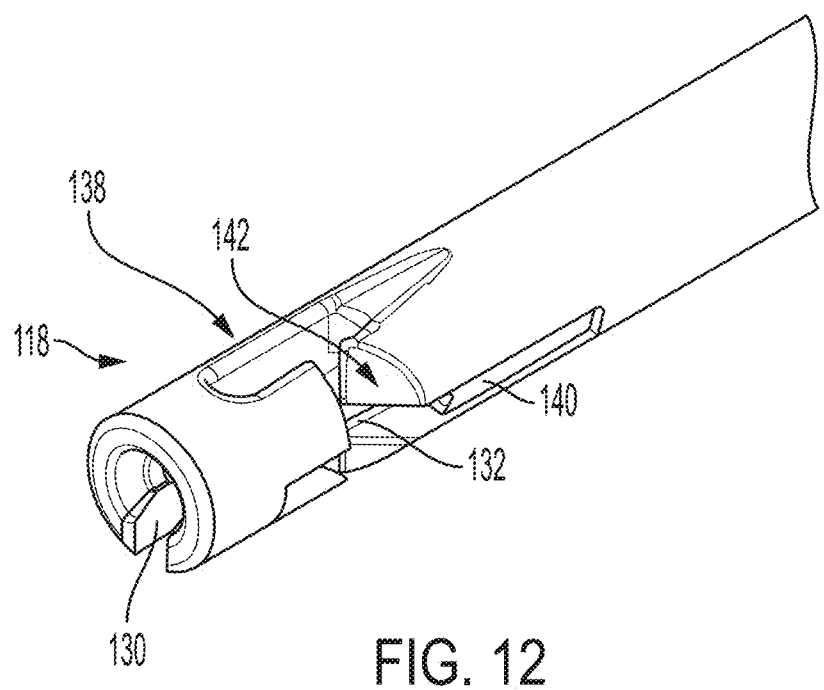
FIG. 12 is a close-up, isometric view schematic representation of the loading zone in a closed position, according to an embodiment.
Figure 13:
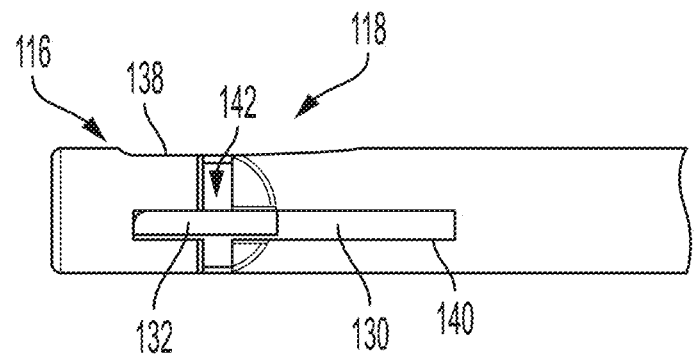
FIG. 13 is a close-up, side view schematic representation of the loading zone in the closed position, according to an embodiment.
Figure 14:
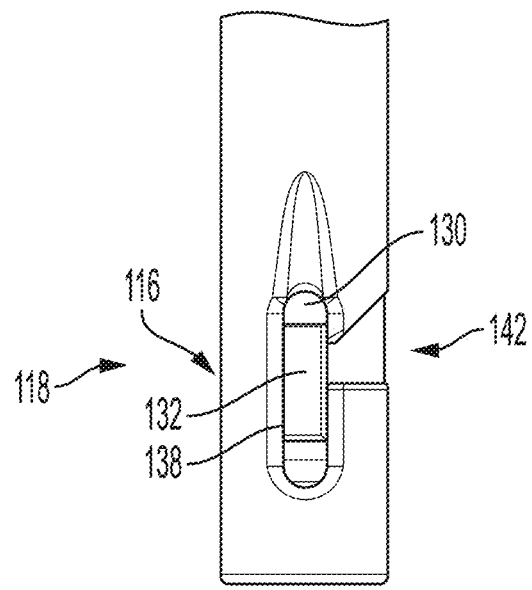
FIG. 14 is a close-up, top view schematic representation of the loading zone in the closed position, according to an embodiment.
Figure 15:
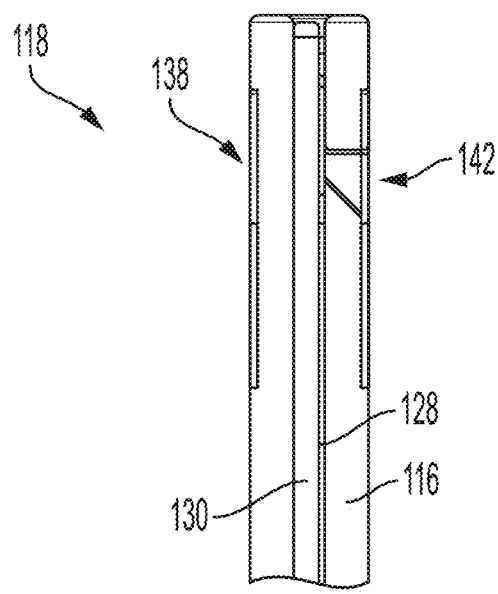
FIG. 15 is a close-up, bottom view schematic representation of he loading zone in the closed position, according to an embodiment.

Turning now to FIG. 12, there is shown a close-up, isometric view schematic representation of the loading zone 118 in a closed position, according to an embodiment. From the open position, the actuator 108 (FIGS. 1-5) is released and slides distally to the closed position. As the actuator 108 slides distally, the gate bar 130 moves distally within the elongated channel 128 to the distal end 104 of the knot pusher 100, as shown in FIG. 15. As the gate bar 130 slides distally, the gate cross bar 132 moves distally to the closed position. In the closed position, the gate cross bar 132 extends into the gate slot 140, as shown in FIGS. 12-13. As also shown in FIGS. 12-13, when the gate cross bar 132 extends into the gate slot 140, the gate cross bar 132 blocks the suture loading slot 142.

Figure 16:
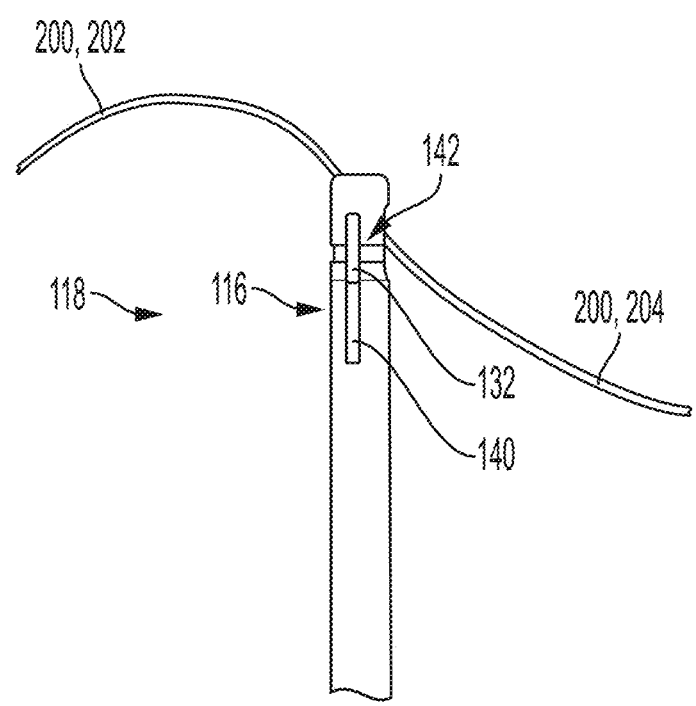
FIG. 16 is a side view of the loading zone in the closed position with suture extending therethrough, according to an embodiment.

Turning now to FIG. 16, there is shown a side view of the loading zone 118 in the closed position with suture 200 extending therethrough, according to an embodiment. As described above, when the actuator 108 is released and moves distally to the closed position, the gate bar 130 moves distally, pushing the gate cross bar 132 distally within the gate slot 140. The gate bar 130 pushes a first limb 202 of the suture 200 through the elongated channel 128 and out of the distal end 104 of the elongated tube 116. A second limb 204 of the suture 200 extends out through the suture exit slot 138 and, in some cases, along the recess 154.

Figure 17:
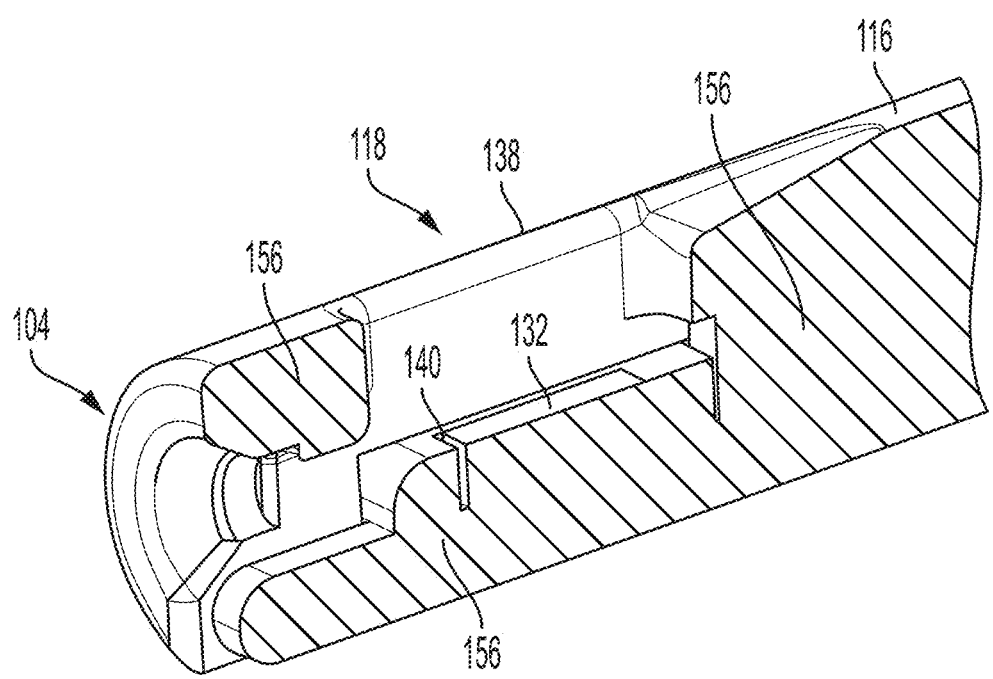
FIG. 17 is a close-up, cross-sectional view schematic representation of the loading zone in the closed position, according to an embodiment.
Figure 18:
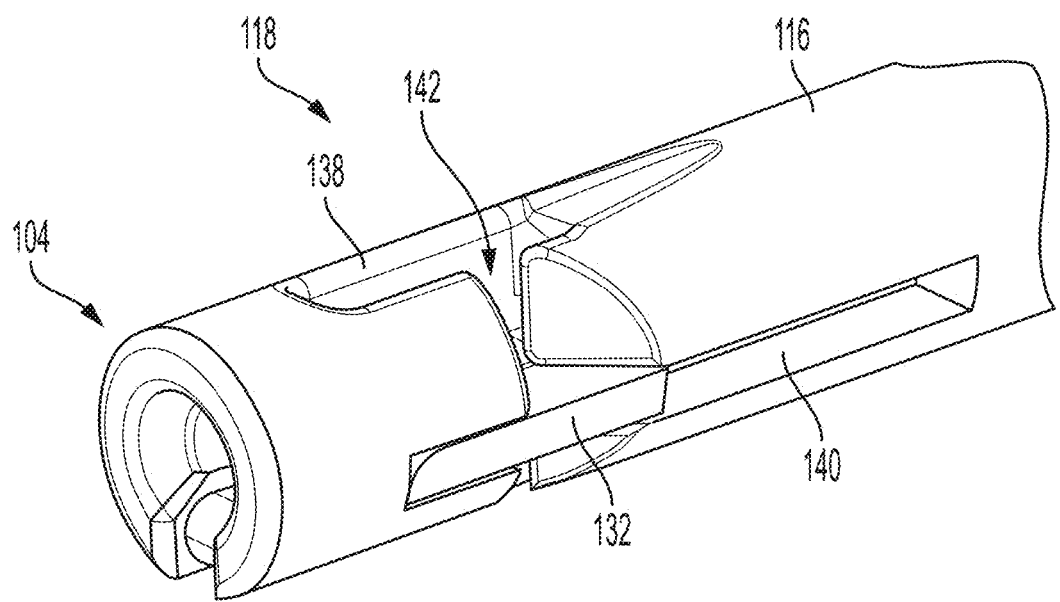
FIG. 18 is a close-up, isometric view schematic representation of the loading zone in the closed position, according to an embodiment.

Turning now to FIG. 17, there is shown a dose-up, cross-sectional view schematic representation of the loading zone 118 in the closed position, according to an embodiment. The path of the suture 200 is shown in FIG. 17. The path of the suture 200 flows from the distal end 104 of the elongated tube 116, over the blocked gate slot 140, and out of the suture exit slot 138. In the depicted embodiment, fillets 156 are on all edges within the elongated tube 116 at the loading zone 118. The fillets 156 ensure that the edges are rounded such that the edges cannot interfere with the suture 200, which could cause fraying. A close-up, isometric view schematic representation of the loading zone 118 in the closed position in shown in FIG. 18. As shown, the gate cross bar 132 is in the closed position within the gate slot 140.

Advantages of this knot pusher 100 include the ability to quickly load suture 200 without needing to thread the distal end 104. The ergonomic loop handle 106 of the knot pusher 100 disclosed herein enforces the correct orientation of the knot pusher 100 for use.

It should be understood that the values used above are only representative values, and other values may be in keeping with the spirit and intention of this disclosure.

While several inventive embodiments have been described and illustrated herein with reference to certain exemplary embodiments, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein (and it will be understood by one skilled in the art that various changes in detail may be effected therein without departing from the spirit and scope of the invention as defined by claims that can be supported by the written description and drawings). More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Further, where exemplary embodiments are described with reference to a certain number of elements it will be understood that the exemplary embodiments can be practiced utilizing either less than or more than the certain number of elements.

All references, including publications, patent applications, and patents, cited herein are hereby incorporated by reference to the same extent as if each reference were individually and specifically indicated to be incorporated by reference and were set forth in its entirety herein.

All definitions, as defined and used herein, should be understood to control over dictionary definitions, definitions in documents incorporated by reference, and/or ordinary meanings of the defined terms.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if not directly attached to where there is something intervening.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A knot pusher, comprising:
   an actuator housing having an actuator moveable between an open position and a closed position;
   a cannulated and elongated tube having an outer surface and an inner surface defining a cannulated space with an inner volume and extending from the actuator housing;
   a gate slot extending through the elongated tube within a gate slot space, wherein the gate slot space extends from a portion of the outer surface to an adjacent portion of the inner surface and is outside of and adjacent to the cannulated space;
   a suture loading slot extending through the elongated tube and traversing the gate slot;
   a gate cross bar moveable within the gate slot and connected to the actuator such that the gate cross bar moves with the actuator between the open position and the closed position;
   wherein when the actuator is in the closed position, the gate cross bar extends through at least a portion of the suture loading slot.

2. The knot pusher of claim 1, further comprising a handle having a ring-shaped end connected to the actuator housing.

3. The knot pusher of claim 1, further comprising an elongated channel extending along and through the elongated tube.

4. The knot pusher of claim 3, further comprising a moveable gate bar connected to the actuator and the gate cross bar.

5. The knot pusher of claim 4, wherein the moveable gate bar is moveable within the elongated channel between the open position and the closed position.

6. The knot pusher of claim 1, wherein the suture loading slot extends in a direction that is substantially perpendicular to a direction in which the gate slot extends.

7. The knot pusher of claim 1, further comprising a spring connecting the actuator to the actuator housing.

8. The knot pusher of claim 7, further comprising an actuator button extending from an outer surface of the actuator and through the actuator housing.

9. The knot pusher of claim 8, wherein the outer surface of the actuator extends at an angle relative to a central longitudinal axis extending through the elongated tube.

10. The knot pusher of claim 9, further comprising a catch on the actuator housing, wherein the outer surface of the actuator engages the catch when the actuator is in the closed position.

11. A knot pusher, comprising:
    an actuator housing having an actuator moveable between an open position and a closed position;
    a cannulated and elongated tube having an outer surface and an inner surface defining a cannulated space with an inner volume and extending from the actuator housing;
    a gate slot extending through the elongated tube within a gate slot space, wherein the gate slot space extends from a portion of the outer surface to an adjacent portion of the inner surface and is outside of and adjacent to the cannulated space;
    a suture exit slot extending through the elongated tube;
    a suture loading slot extending through the elongated tube and traversing the gate slot;
    a gate cross bar moveable within the gate slot and connected to the actuator such that the gate cross bar moves with the actuator between the open position and the closed position;
    wherein when the actuator is in the closed position, the gate cross bar extends through at least a portion of the suture loading slot.

12. The knot pusher of claim 11, wherein the suture exit slot is 90 degrees from the gate slot.

13. The knot pusher of claim 11, wherein the suture exit slot extends to a recess in the elongated tube.

14. The knot pusher of claim 11, wherein the suture loading slot extends to the suture exit slot.

15. The knot pusher of claim 11, further comprising an elongated channel extending along and through the elongated tube, wherein the elongated channel is substantially parallel to the suture exit slot.

16. The knot pusher of claim 11, wherein in the closed position, suture extends through a distal end of the elongated tube and through the suture exit slot.

17. The knot pusher of claim 11, further comprising one or more fillet edges within the actuator housing.

18. A knot pusher, comprising:
    a handle having an actuator housing extending from a ring-shaped end;
    an actuator at least partially within the actuator housing and moveable between an open position and a closed position;
    a cannulated and elongated tube having an outer surface and an inner surface defining a cannulated space with an inner volume and extending from the actuator housing;
    a gate slot extending through the elongated tube within a gate slot space, wherein the gate slot space extends from a portion of the outer surface to an adjacent portion of the inner surface and is outside of and adjacent to the cannulated space;
    a suture loading slot extending through the elongated tube and traversing the gate slot;

a gate cross bar moveable within the gate slot and connected to the actuator such that the gate cross bar moves with the actuator between the open position and the closed position;

wherein when the actuator is in the closed position, the gate cross bar extends through at least a portion of the suture loading slot.

19. The knot pusher of claim 11, wherein ring-shaped end angled relative to a central longitudinal axis extending through the elongated tube.

20. The knot pusher of claim 19, wherein a central axis extending through an aperture in the ring-shaped end is at an acute angle relative to the central longitudinal axis extending through the elongated tube.

* * * * *